United States Patent
Hatrick et al.

(10) Patent No.: US 11,241,042 B2
(45) Date of Patent: Feb. 8, 2022

(54) HEATING SMOKEABLE MATERIAL

(71) Applicant: British American Tobacco (Investments) Limited, London (GB)

(72) Inventors: David Hatrick, London (GB); Simon Brereton, London (GB)

(73) Assignee: Nicoventures Trading Limited, London (GB)

( * ) Notice: Subject to any disclaimer, the term of this patent is extended or adjusted under 35 U.S.C. 154(b) by 368 days.

(21) Appl. No.: 14/428,626

(22) PCT Filed: Sep. 11, 2013

(86) PCT No.: PCT/EP2013/068797
§ 371 (c)(1),
(2) Date: Mar. 16, 2015

(87) PCT Pub. No.: WO2014/048745
PCT Pub. Date: Apr. 3, 2014

(65) Prior Publication Data
US 2015/0272219 A1    Oct. 1, 2015

(30) Foreign Application Priority Data

Sep. 25, 2012 (GB) .................................. 1217067.6

(51) Int. Cl.
*A24F 40/465* (2020.01)
*A24F 47/00* (2020.01)
(Continued)

(52) U.S. Cl.
CPC ............ *A24F 40/465* (2020.01); *A24F 40/20* (2020.01); *A61M 11/044* (2014.02); *A61M 15/06* (2013.01)

(58) Field of Classification Search
CPC .... A24F 47/008; A24F 47/004; A24F 47/002; A24F 47/00; A24F 40/465;
(Continued)

(56) References Cited

U.S. PATENT DOCUMENTS 219,628 A   9/1879  Edison
219,634 A   9/1879  Gifford
(Continued)

FOREIGN PATENT DOCUMENTS

AT    262137 B    5/1968
AT    306224 B    3/1973
(Continued)

OTHER PUBLICATIONS

University of Illinois, Scientific Principles, Accessed Jun. 15, 2017, <matse1.matse.illinois.edu>.*

(Continued)

*Primary Examiner* — Michael J Felton
*Assistant Examiner* — Sonny V Nguyen
(74) *Attorney, Agent, or Firm* — Patterson Thuente Pedersen, P.A.

(57) ABSTRACT

An apparatus configured to volatilize components of smokable material for inhalation, comprising a smokable material heating chamber and a heating material which is configured to be heated by the presence of a varying magnetic field, wherein the heating material is arranged to transfer heat energy to smokable material in the heating chamber to volatilize said components.

11 Claims, 2 Drawing Sheets

(51) Int. Cl.
*A61M 15/06* (2006.01)
*A61M 11/04* (2006.01)
*A24F 40/20* (2020.01)

(58) Field of Classification Search
CPC .............. A61M 11/041; A61M 11/042; A61M 11/044; A61M 15/06
See application file for complete search history.

(56) References Cited

U.S. PATENT DOCUMENTS

| | | |
|---|---|---|
| 219,635 A | 9/1879 | Giles |
| 219,643 A | 9/1879 | Mattoni |
| 2,462,563 A | 2/1949 | Seyforth |
| 2,689,150 A | 9/1954 | Croce |
| 2,888,208 A | 5/1959 | Fedit |
| 3,040,991 A | 6/1962 | Fedit |
| 3,043,524 A | 7/1962 | Boris |
| 3,144,174 A | 8/1964 | Abplanalp |
| 3,258,015 A | 6/1966 | Ellis et al. |
| 3,289,949 A | 12/1966 | Roth |
| 3,347,231 A | 10/1967 | Chang |
| 3,522,806 A | 8/1970 | Szekely |
| 3,647,143 A | 3/1972 | Gauthier et al. |
| 3,658,059 A | 4/1972 | Steil |
| 3,733,010 A | 5/1973 | Riccio |
| 3,856,185 A | 12/1974 | Riccio |
| 3,864,326 A | 2/1975 | Babington et al. |
| 3,913,843 A | 10/1975 | Cambio, Jr. |
| 3,943,942 A | 3/1976 | Anderson |
| 4,017,701 A | 4/1977 | Mittelmann |
| 4,149,548 A | 4/1979 | Bradshaw |
| 4,284,089 A | 8/1981 | Ray |
| 4,299,274 A | 11/1981 | Campbell et al. |
| 4,299,355 A | 11/1981 | Hakkinen |
| 4,303,541 A | 12/1981 | Wasel-Nielen et al. |
| 4,393,884 A | 7/1983 | Jacobs |
| 4,429,835 A | 2/1984 | Brugger et al. |
| 4,746,067 A | 5/1988 | Svoboda |
| 4,765,347 A | 8/1988 | Sensabaugh, Jr. et al. |
| 4,765,348 A | 8/1988 | Honeycutt |
| 4,771,795 A | 9/1988 | White et al. |
| 4,776,353 A | 10/1988 | Lilja et al. |
| 4,819,665 A | 4/1989 | Roberts et al. |
| 4,827,950 A | 5/1989 | Banerjee et al. |
| 4,907,606 A | 3/1990 | Lilja |
| 4,913,168 A | 4/1990 | Potter et al. |
| 4,917,119 A | 4/1990 | Potter et al. |
| 4,917,120 A | 4/1990 | Hill |
| 4,924,883 A | 5/1990 | Perfetti et al. |
| 4,938,236 A | 7/1990 | Banerjee et al. |
| 4,941,483 A | 7/1990 | Ridings et al. |
| 4,947,874 A | 8/1990 | Brooks et al. |
| 4,955,399 A | 9/1990 | Potter et al. |
| 4,979,521 A | 12/1990 | Davis et al. |
| 4,987,291 A | 1/1991 | McGaffigan et al. |
| 4,991,606 A | 2/1991 | Serrano |
| 5,019,122 A | 5/1991 | Clearman et al. |
| 5,020,509 A | 6/1991 | Suzuki et al. |
| 5,040,552 A | 8/1991 | Schleich et al. |
| 5,042,509 A | 8/1991 | Banerjee et al. |
| 5,060,667 A | 10/1991 | Strubel |
| 5,060,671 A | 10/1991 | Counts et al. |
| 5,076,292 A | 12/1991 | Sensabaugh et al. |
| 5,080,115 A | 1/1992 | Templeton |
| 5,093,894 A | 3/1992 | Deevi et al. |
| 5,095,921 A | 3/1992 | Losee et al. |
| 5,097,850 A | 3/1992 | Braunshteyn et al. |
| 5,099,861 A | 3/1992 | Clearman et al. |
| 5,105,831 A | 4/1992 | Banerjee et al. |
| 5,119,834 A | 6/1992 | Shannon et al. |
| 5,133,368 A | 7/1992 | Neumann |
| 5,144,962 A | 9/1992 | Counts et al. |
| 5,146,934 A | 9/1992 | Deevi et al. |
| 5,159,940 A | 11/1992 | Hayward et al. |
| 5,167,242 A | 12/1992 | Turner et al. |
| 5,179,966 A | 1/1993 | Losee et al. |
| 5,188,130 A | 2/1993 | Hajaligol et al. |
| 5,224,498 A | 7/1993 | Deevi |
| 5,230,715 A | 7/1993 | Iizuna |
| 5,235,992 A | 8/1993 | Sensabaugh, Jr. |
| 5,249,586 A | 10/1993 | Morgan |
| 5,261,424 A | 11/1993 | Sprinkel |
| 5,269,327 A | 12/1993 | Counts et al. |
| 5,272,216 A | 12/1993 | Clark, Jr. et al. |
| 5,285,798 A | 2/1994 | Banerjee et al. |
| 5,293,883 A | 3/1994 | Edwards |
| 5,312,046 A | 5/1994 | Knoch et al. |
| 5,322,075 A | 6/1994 | Deevi |
| 5,327,915 A | 7/1994 | Porenski et al. |
| 5,345,951 A | 9/1994 | Serrano |
| 5,357,984 A | 10/1994 | Farrier et al. |
| 5,369,723 A | 11/1994 | Counts et al. |
| 5,396,911 A | 3/1995 | Casey et al. |
| 5,400,808 A | 3/1995 | Turner et al. |
| 5,408,574 A | 4/1995 | Deevi et al. |
| 5,412,183 A | 5/1995 | Buffenoir et al. |
| 5,415,186 A | 5/1995 | Casey et al. |
| 5,443,560 A | 8/1995 | Deevi et al. |
| 5,454,363 A | 10/1995 | Sata |
| 5,461,695 A | 10/1995 | Knoch |
| 5,474,059 A | 12/1995 | Cooper |
| 5,483,953 A | 1/1996 | Cooper |
| 5,499,636 A | 3/1996 | Baggett, Jr. et al. |
| 5,500,511 A | 3/1996 | Hansen et al. |
| 5,501,236 A | 3/1996 | Hill et al. |
| 5,502,743 A | 3/1996 | Conochie et al. |
| 5,511,538 A | 4/1996 | Haber et al. |
| 5,517,981 A | 5/1996 | Taub et al. |
| 5,534,020 A | 7/1996 | Cheney, III |
| 5,538,020 A | 7/1996 | Farrier |
| 5,549,906 A | 8/1996 | Santus |
| 5,564,442 A | 10/1996 | MacDonald et al. |
| 5,591,368 A | 1/1997 | Fleischhauer |
| 5,593,792 A | 1/1997 | Farrier et al. |
| 5,613,505 A | 3/1997 | Campbell |
| 5,645,749 A | 7/1997 | Wang |
| 5,649,554 A | 7/1997 | Sprinkel |
| 5,659,656 A | 8/1997 | Das |
| 5,687,912 A | 11/1997 | Denyer |
| 5,699,786 A | 12/1997 | Oshima et al. |
| 5,711,292 A | 1/1998 | Hammarlund |
| 5,726,421 A | 3/1998 | Fleischhauer |
| 5,736,110 A | 4/1998 | Angelillo et al. |
| 5,778,899 A | 7/1998 | Saito et al. |
| 5,837,088 A | 11/1998 | Palmgren |
| 5,845,649 A | 12/1998 | Saito et al. |
| 5,865,185 A | 2/1999 | Collins |
| 5,865,186 A | 2/1999 | Volsey, II |
| 5,878,752 A | 3/1999 | Morris |
| 5,902,501 A | 5/1999 | Nunnally |
| 5,921,233 A | 7/1999 | Gold et al. |
| 5,935,486 A | 8/1999 | Bell et al. |
| 5,938,125 A | 8/1999 | Ritsche et al. |
| 6,000,394 A | 12/1999 | Blaha-Schnabel |
| 6,026,820 A | 2/2000 | Baggett |
| 6,041,790 A | 3/2000 | Smith et al. |
| 6,053,176 A | 4/2000 | Adams |
| 6,079,405 A | 6/2000 | Justo |
| 6,085,741 A | 7/2000 | Becker |
| 6,089,857 A | 7/2000 | Matsuura et al. |
| 6,113,078 A | 9/2000 | Rock |
| 6,125,853 A | 10/2000 | Susa et al. |
| 6,129,080 A | 10/2000 | Pitcher et al. |
| 6,158,676 A | 12/2000 | Hughes |
| 6,164,287 A | 12/2000 | White |
| 6,178,963 B1 | 1/2001 | Baik |
| 6,209,457 B1 | 4/2001 | Kenworthy et al. |
| 6,223,745 B1 | 5/2001 | Hammarlund et al. |
| 6,230,703 B1 | 5/2001 | Bono |
| 6,234,459 B1 | 5/2001 | Rock |
| 6,244,573 B1 | 6/2001 | Rock |
| 6,248,257 B1 | 6/2001 | Bell et al. |
| 6,267,110 B1 | 7/2001 | Tenenboum et al. |

(56) References Cited

U.S. PATENT DOCUMENTS

| | | |
|---|---|---|
| 6,283,116 B1 | 9/2001 | Yang |
| 6,289,889 B1 | 9/2001 | Bell et al. |
| 6,297,483 B2 | 10/2001 | Sadahira et al. |
| 6,347,789 B1 | 2/2002 | Rock |
| 6,427,878 B1 | 8/2002 | Greiner-Perth et al. |
| 6,595,209 B1 | 7/2003 | Rose et al. |
| 6,598,607 B2 | 7/2003 | Adiga et al. |
| 6,648,306 B2 | 11/2003 | Rock |
| 6,669,176 B2 | 12/2003 | Rock |
| 6,708,846 B1 | 3/2004 | Fuchs et al. |
| 6,761,164 B2 | 7/2004 | Amirpour et al. |
| 6,769,436 B2 | 8/2004 | Horian |
| 6,799,572 B2 | 10/2004 | Nichols et al. |
| 6,803,545 B2 | 10/2004 | Blake et al. |
| 6,803,550 B2 | 10/2004 | Sharpe |
| 6,886,556 B2 | 5/2005 | Fuchs |
| 6,968,888 B2 | 11/2005 | Kolowich |
| 6,994,096 B2 | 2/2006 | Rostami |
| 7,041,123 B2 | 5/2006 | Stapf et al. |
| 7,077,130 B2 | 7/2006 | Nichols et al. |
| 7,081,211 B2 | 7/2006 | Li et al. |
| 7,088,914 B2 | 8/2006 | Whittle et al. |
| 7,163,014 B2 | 1/2007 | Nichols et al. |
| 7,185,659 B2 | 3/2007 | Sharpe |
| 7,234,459 B2 | 6/2007 | Del Bon |
| 7,235,187 B2 | 6/2007 | Li et al. |
| 7,290,549 B2 | 11/2007 | Banerjee et al. |
| 7,303,328 B2 | 12/2007 | Faraldi et al. |
| 7,335,186 B2 | 2/2008 | O'Neil |
| 7,373,938 B2 | 5/2008 | Nichols et al. |
| 7,434,584 B2 | 10/2008 | Steinberg |
| 7,458,374 B2 | 12/2008 | Hale et al. |
| 7,540,286 B2 | 6/2009 | Cross et al. |
| 7,581,540 B2 | 9/2009 | Hale et al. |
| 7,581,718 B1 | 9/2009 | Chang |
| 7,585,493 B2 | 9/2009 | Hale et al. |
| 7,645,442 B2 | 1/2010 | Hale et al. |
| 7,665,461 B2 | 2/2010 | Zierenberg et al. |
| 7,832,397 B2 | 11/2010 | Lipowicz |
| 7,834,295 B2 | 11/2010 | Sharma et al. |
| 7,987,846 B2 | 8/2011 | Hale et al. |
| 8,156,944 B2 | 4/2012 | Han |
| 8,342,184 B2 | 1/2013 | Inagaki et al. |
| 8,365,742 B2 | 2/2013 | Hon |
| 8,375,957 B2 | 2/2013 | Hon |
| 8,402,976 B2 | 3/2013 | Fernando |
| 8,439,046 B2 | 5/2013 | Peters |
| 8,459,271 B2 | 6/2013 | Inagaki |
| 8,689,804 B2 | 4/2014 | Fernando |
| 8,689,805 B2 | 4/2014 | Hon |
| 8,701,682 B2 | 4/2014 | Sherwood |
| 8,707,967 B2 | 4/2014 | Li |
| 9,084,440 B2 | 7/2015 | Zuber |
| 9,125,437 B2 | 9/2015 | Kaljura |
| 9,302,522 B2 | 4/2016 | Sherwood |
| 9,439,454 B2 | 9/2016 | Fernando |
| 9,668,516 B2 | 6/2017 | Sherwood |
| 9,955,726 B2 | 5/2018 | Brinkley |
| 10,130,121 B2 | 11/2018 | Plojoux |
| 10,130,780 B2 | 11/2018 | Talon |
| 2001/0042927 A1 | 11/2001 | Rock |
| 2001/0054421 A1 | 12/2001 | Jaser et al. |
| 2002/0043260 A1 | 4/2002 | Layer et al. |
| 2002/0078951 A1 | 6/2002 | Nichols et al. |
| 2002/0078955 A1 | 6/2002 | Nichols et al. |
| 2002/0078956 A1 | 6/2002 | Sharpe |
| 2002/0089072 A1 | 7/2002 | Rock |
| 2002/0121624 A1 | 9/2002 | Usui |
| 2003/0007887 A1 | 1/2003 | Roumpos |
| 2003/0052196 A1 | 3/2003 | Fuchs |
| 2003/0097164 A1 | 5/2003 | Stapf et al. |
| 2003/0101984 A1 | 6/2003 | Li |
| 2003/0105192 A1 | 6/2003 | Li et al. |
| 2003/0106551 A1 | 6/2003 | Sprinkel, Jr. et al. |
| 2003/0111637 A1 | 6/2003 | Li et al. |
| 2003/0159702 A1 | 8/2003 | Lindell et al. |
| 2003/0209240 A1 | 11/2003 | Hale et al. |
| 2003/0217750 A1 | 11/2003 | Amirpour et al. |
| 2003/0226837 A1 | 12/2003 | Blake et al. |
| 2003/0230567 A1 | 12/2003 | Centanni |
| 2004/0031495 A1 | 2/2004 | Steinberg |
| 2004/0065314 A1 | 4/2004 | Layer et al. |
| 2004/0068222 A1 | 4/2004 | Brian |
| 2004/0083755 A1 | 5/2004 | Kolowich |
| 2004/0149297 A1 | 8/2004 | Sharpe |
| 2004/0177849 A1 | 9/2004 | Del Bon |
| 2004/0234699 A1 | 11/2004 | Hale et al. |
| 2004/0234914 A1 | 11/2004 | Hale et al. |
| 2004/0234916 A1 | 11/2004 | Hale et al. |
| 2004/0255941 A1 | 12/2004 | Nichols et al. |
| 2004/0261782 A1 | 12/2004 | Furumichi et al. |
| 2005/0007870 A1 | 1/2005 | Faraldi et al. |
| 2005/0016549 A1 | 1/2005 | Banerjee et al. |
| 2005/0025213 A1 | 2/2005 | Parks |
| 2005/0045193 A1 | 3/2005 | Yang |
| 2005/0063686 A1 | 3/2005 | Whittle et al. |
| 2005/0079166 A1 | 4/2005 | Damani et al. |
| 2005/0098187 A1 | 5/2005 | Grierson et al. |
| 2005/0133029 A1 | 6/2005 | Nichols et al. |
| 2005/0196345 A1 | 9/2005 | Diederichs et al. |
| 2005/0236006 A1 | 10/2005 | Cowan |
| 2006/0027233 A1 | 2/2006 | Zierenberg et al. |
| 2006/0032501 A1 | 2/2006 | Hale et al. |
| 2006/0043067 A1 | 3/2006 | Kadkhodayan |
| 2006/0102175 A1 | 5/2006 | Nelson |
| 2006/0118128 A1 | 6/2006 | Hoffman |
| 2006/0137681 A1 | 6/2006 | Von Hollen et al. |
| 2006/0191546 A1 | 8/2006 | Takano |
| 2006/0196518 A1 | 9/2006 | Hon |
| 2006/0196885 A1 | 9/2006 | Leach et al. |
| 2006/0255029 A1 | 11/2006 | Bone, Jr. |
| 2007/0023043 A1 | 2/2007 | Von Hollen et al. |
| 2007/0028916 A1 | 2/2007 | Hale et al. |
| 2007/0031340 A1 | 2/2007 | Hale et al. |
| 2007/0102533 A1 | 5/2007 | Rosell et al. |
| 2007/0125362 A1 | 6/2007 | Ford et al. |
| 2007/0131219 A1 | 6/2007 | Ford et al. |
| 2007/0138207 A1 | 6/2007 | Bonney et al. |
| 2007/0175476 A1 | 8/2007 | Lipowicz |
| 2007/0204864 A1 | 9/2007 | Grychowski et al. |
| 2007/0222112 A1 | 9/2007 | Christ et al. |
| 2007/0235046 A1 | 10/2007 | Gedevanishvili |
| 2007/0267407 A1 | 11/2007 | Loveless et al. |
| 2007/0283972 A1 | 12/2007 | Monsees et al. |
| 2007/0289720 A1 | 12/2007 | Sunol et al. |
| 2008/0027694 A1 | 1/2008 | Gitman |
| 2008/0031267 A1 | 2/2008 | Imao |
| 2008/0038363 A1 | 2/2008 | Zaffaroni et al. |
| 2008/0149118 A1* | 6/2008 | Oglesby ............... A61M 11/047 131/194 |
| 2008/0156326 A1 | 7/2008 | Belcastro et al. |
| 2008/0216828 A1 | 9/2008 | Wensley et al. |
| 2008/0241255 A1 | 10/2008 | Rose et al. |
| 2008/0257367 A1 | 10/2008 | Paterno et al. |
| 2008/0276947 A1 | 11/2008 | Martzel |
| 2008/0312674 A1 | 12/2008 | Chen et al. |
| 2009/0015717 A1 | 1/2009 | Arnao et al. |
| 2009/0071477 A1 | 3/2009 | Hale et al. |
| 2009/0078711 A1 | 3/2009 | Farone et al. |
| 2009/0090349 A1 | 4/2009 | Donovan |
| 2009/0090351 A1 | 4/2009 | Sunol et al. |
| 2009/0095287 A1 | 4/2009 | Emarlou |
| 2009/0107492 A1 | 4/2009 | Ooida |
| 2009/0114215 A1 | 5/2009 | Boeck et al. |
| 2009/0127253 A1* | 5/2009 | Stark .................. B29C 35/0272 219/660 |
| 2009/0151717 A1 | 6/2009 | Bowen et al. |
| 2009/0162294 A1 | 6/2009 | Werner |
| 2009/0180968 A1 | 7/2009 | Hale et al. |
| 2009/0199843 A1 | 8/2009 | Farone et al. |
| 2009/0217923 A1 | 9/2009 | Boehm et al. |
| 2009/0230117 A1 | 9/2009 | Fernando et al. |
| 2009/0255923 A1 | 10/2009 | Buehrer et al. |
| 2009/0260641 A1 | 10/2009 | Monsees et al. |

(56) References Cited

U.S. PATENT DOCUMENTS

| | | |
|---|---|---|
| 2009/0260642 A1 | 10/2009 | Monsees et al. |
| 2009/0280043 A1 | 11/2009 | Ferguson |
| 2009/0301363 A1 | 12/2009 | Damani et al. |
| 2009/0301471 A1 | 12/2009 | Stirzel |
| 2009/0302019 A1 | 12/2009 | Selenski et al. |
| 2010/0006092 A1 | 1/2010 | Hale et al. |
| 2010/0025023 A1 | 2/2010 | Schmidt et al. |
| 2010/0031968 A1 | 2/2010 | Sheikh et al. |
| 2010/0043809 A1 | 2/2010 | Magnon |
| 2010/0065052 A1 | 3/2010 | Sharma et al. |
| 2010/0068154 A1 | 3/2010 | Sharma et al. |
| 2010/0089381 A1 | 4/2010 | Bolmer et al. |
| 2010/0181387 A1 | 7/2010 | Zaffaroni et al. |
| 2010/0236546 A1 | 9/2010 | Yamada et al. |
| 2010/0242974 A1 | 9/2010 | Pan |
| 2010/0258585 A1 | 10/2010 | Jamison |
| 2010/0268212 A1 | 10/2010 | Manwaring et al. |
| 2010/0300467 A1 | 12/2010 | Kuistila et al. |
| 2010/0307518 A1 | 12/2010 | Wang |
| 2010/0313901 A1 | 12/2010 | Fernando et al. |
| 2011/0005535 A1 | 1/2011 | Xiu |
| 2011/0030671 A1 | 2/2011 | Ferguson et al. |
| 2011/0126848 A1 | 6/2011 | Zuber et al. |
| 2011/0192408 A1 | 8/2011 | Inagaki et al. |
| 2011/0240022 A1 | 10/2011 | Hodges |
| 2011/0283458 A1 | 11/2011 | Gillette et al. |
| 2011/0290266 A1 | 12/2011 | Koeller et al. |
| 2011/0303230 A1* | 12/2011 | Thiry .................. A24C 5/06 131/81.1 |
| 2012/0006342 A1 | 1/2012 | Rose et al. |
| 2012/0006343 A1 | 1/2012 | Renaud et al. |
| 2012/0145189 A1 | 6/2012 | Knopow et al. |
| 2012/0234315 A1* | 9/2012 | Li .................. A24F 47/008 128/200.21 |
| 2013/0061861 A1 | 3/2013 | Hearn |
| 2013/0133675 A1 | 5/2013 | Shinozaki |
| 2013/0152922 A1 | 6/2013 | Benassayag et al. |
| 2014/0196716 A1 | 7/2014 | Liu |
| 2014/0216482 A1 | 8/2014 | Dotan |
| 2014/0238737 A1 | 8/2014 | Backman |
| 2015/0245669 A1 | 9/2015 | Cadieux et al. |
| 2015/0272219 A1 | 10/2015 | Hatrick |
| 2015/0282256 A1 | 10/2015 | Iguro et al. |
| 2015/0302971 A1 | 10/2015 | Wagman et al. |
| 2015/0320116 A1 | 11/2015 | Bleloch et al. |
| 2016/0036222 A1 | 2/2016 | Templeton et al. |
| 2016/0044963 A1 | 2/2016 | Saleem |
| 2016/0150825 A1 | 6/2016 | Mironov |
| 2016/0150828 A1 | 6/2016 | Goldstein et al. |
| 2017/0055574 A1 | 3/2017 | Kaufman et al. |
| 2017/0055575 A1 | 3/2017 | Wilke et al. |
| 2017/0055580 A1 | 3/2017 | Blandino et al. |
| 2017/0055581 A1 | 3/2017 | Wilke et al. |
| 2017/0055582 A1 | 3/2017 | Blandino et al. |
| 2017/0055583 A1 | 3/2017 | Blandino et al. |
| 2017/0055584 A1 | 3/2017 | Blandino et al. |
| 2017/0071250 A1 | 3/2017 | Mironov |
| 2017/0079325 A1 | 3/2017 | Mironov |
| 2017/0086508 A1 | 3/2017 | Mironov et al. |
| 2017/0119046 A1 | 5/2017 | Kaufman et al. |
| 2017/0119047 A1 | 5/2017 | Blandino et al. |
| 2017/0119048 A1 | 5/2017 | Kaufman et al. |
| 2017/0119049 A1 | 5/2017 | Blandino et al. |
| 2017/0119050 A1 | 5/2017 | Blandino et al. |
| 2017/0119051 A1 | 5/2017 | Blandino et al. |
| 2017/0119054 A1 | 5/2017 | Zinovik et al. |
| 2017/0156403 A1 | 6/2017 | Gill et al. |
| 2018/0235279 A1 | 8/2018 | Wilke |
| 2018/0242633 A1 | 8/2018 | Wilke et al. |
| 2018/0242636 A1 | 8/2018 | Blandino |
| 2018/0249760 A1 | 9/2018 | Kaufman et al. |
| 2018/0279677 A1 | 10/2018 | Blandino et al. |
| 2018/0317552 A1 | 11/2018 | Kaufman |
| 2018/0317553 A1 | 11/2018 | Blandino |
| 2018/0317554 A1 | 11/2018 | Kaufman et al. |
| 2018/0317555 A1 | 11/2018 | Blandino et al. |
| 2018/0325173 A1 | 11/2018 | Blandino et al. |
| 2019/0082738 A1 | 3/2019 | Blandino et al. |
| 2019/0191780 A1 | 6/2019 | Wilke et al. |
| 2019/0230988 A1 | 8/2019 | Aoun |
| 2019/0239555 A1 | 8/2019 | Nicholson |
| 2019/0313695 A1 | 10/2019 | Kaufman et al. |
| 2019/0364973 A1 | 12/2019 | Kaufman |
| 2020/0054068 A1 | 2/2020 | Blandino et al. |
| 2020/0054069 A1 | 2/2020 | Blandino et al. |
| 2020/0229497 A1 | 7/2020 | Aoun et al. |
| 2020/0268053 A1 | 8/2020 | Thorsen et al. |
| 2020/0288774 A1 | 9/2020 | Blandino et al. |
| 2020/0352237 A1 | 11/2020 | Kaufman et al. |
| 2021/0137167 A1 | 5/2021 | Aoun et al. |

FOREIGN PATENT DOCUMENTS

| | | |
|---|---|---|
| AT | 321190 B | 3/1975 |
| AT | 321191 B | 3/1975 |
| AU | 2002364521 A1 | 6/2003 |
| CA | 2160990 | 10/1994 |
| CA | 2146954 A1 | 10/1996 |
| CA | 2414161 A1 | 1/2002 |
| CA | 2414191 A1 | 1/2002 |
| CA | 2520759 A1 | 10/2004 |
| CA | 2492255 A1 | 7/2006 |
| CA | 2668465 A1 | 5/2009 |
| CA | 2641869 A1 | 6/2010 |
| CA | 2862048 | 7/2013 |
| CA | 2923377 A1 | 6/2015 |
| CH | 513656 A | 10/1971 |
| CH | 698603 B1 | 9/2009 |
| CL | 2017003408 A1 | 6/2018 |
| CN | 1038085 A | 12/1989 |
| CN | 1043076 A | 6/1990 |
| CN | 1045691 A | 10/1990 |
| CN | 1059649 A | 3/1992 |
| CN | 2144261 Y | 10/1993 |
| CN | 1121385 | 4/1996 |
| CN | 1123000 A | 5/1996 |
| CN | 1123001 A | 5/1996 |
| CN | 1126426 | 7/1996 |
| CN | 1126426 A | 7/1996 |
| CN | 1158757 A | 9/1997 |
| CN | 1195270 A | 10/1998 |
| CN | 1209731 | 3/1999 |
| CN | 1287890 A | 3/2001 |
| CN | 1293591 A | 5/2001 |
| CN | 1293596 A | 5/2001 |
| CN | 1130109 C | 12/2003 |
| CN | 1130137 C | 12/2003 |
| CN | 1151739 C | 6/2004 |
| CN | 1575135 A | 2/2005 |
| CN | 1641976 A | 7/2005 |
| CN | 201076006 | 6/2008 |
| CN | 101277622 | 10/2008 |
| CN | 101390659 | 3/2009 |
| CN | 201199922 | 3/2009 |
| CN | 201445686 U | 5/2010 |
| CN | 101925309 A | 12/2010 |
| CN | 102212340 A | 10/2011 |
| CN | 102483237 A | 5/2012 |
| CN | 102499466 A | 6/2012 |
| CN | 202351223 U | 7/2012 |
| CN | 203369386 | 5/2013 |
| CN | 204091003 | 5/2013 |
| CN | 103689812 | 12/2013 |
| CN | 203369386 | 1/2014 |
| CN | 103608619 A | 2/2014 |
| CN | 103689812 | 4/2014 |
| CN | 103689815 A | 4/2014 |
| CN | 103763954 A | 4/2014 |
| CN | 103974640 A | 8/2014 |
| CN | 103997922 A | 8/2014 |
| CN | 104010531 A | 8/2014 |
| CN | 203748673 U | 8/2014 |
| CN | 203761188 U | 8/2014 |
| CN | 203762288 | 8/2014 |

(56) References Cited

FOREIGN PATENT DOCUMENTS

| | | |
|---|---|---|
| CN | 203762288 U | 8/2014 |
| CN | 104039183 A | 9/2014 |
| CN | 104095291 A | 10/2014 |
| CN | 104095293 A | 10/2014 |
| CN | 104095295 A | 10/2014 |
| CN | 203952405 U | 11/2014 |
| CN | 104203016 A | 12/2014 |
| CN | 104223359 | 12/2014 |
| CN | 104256899 A | 1/2015 |
| CN | 204091003 | 1/2015 |
| CN | 104619202 A | 5/2015 |
| CN | 104664608 A | 6/2015 |
| CN | 104720121 A | 6/2015 |
| CN | 204949521 | 8/2015 |
| CN | 106617325 A | 5/2017 |
| DE | 360431 | 10/1922 |
| DE | 1100884 B | 3/1961 |
| DE | 1425872 A1 | 11/1968 |
| DE | 1290499 B | 3/1969 |
| DE | 1813993 A1 | 6/1970 |
| DE | 1425871 B1 | 10/1970 |
| DE | 2315789 A1 | 10/1973 |
| DE | 4105370 A1 | 8/1992 |
| DE | 4307144 C2 | 1/1995 |
| DE | 4343578 A1 | 6/1995 |
| DE | 29509286 U1 | 10/1995 |
| DE | 4420366 A1 | 12/1995 |
| DE | 29700307 U1 | 5/1997 |
| DE | 19854007 A1 | 5/2000 |
| DE | 19854009 A1 | 5/2000 |
| DE | 10058642 A1 | 6/2001 |
| DE | 10007521 A1 | 8/2001 |
| DE | 10064288 A1 | 8/2001 |
| DE | 10164587 A1 | 7/2003 |
| DE | 102005024803 A1 | 6/2006 |
| DE | 202006013439 U1 | 11/2006 |
| DE | 102005056885 A1 | 5/2007 |
| DE | 102006041544 A1 | 8/2007 |
| DE | 102006041042 A1 | 3/2008 |
| DE | 102006047146 A1 | 4/2008 |
| DE | 102007011120 A1 | 9/2008 |
| DE | 102008034509 A1 | 4/2009 |
| DE | 102008013303 A1 | 9/2009 |
| DE | 202009010400 U1 | 12/2009 |
| DE | 102008038121 A1 | 2/2010 |
| DE | 202010011436 U1 | 12/2010 |
| DK | 114399 B | 6/1969 |
| DK | 488488 A | 3/1989 |
| DK | 540774 T3 | 7/1995 |
| DK | 540775 T3 | 8/1997 |
| EP | 33668 A1 | 8/1981 |
| EP | 0033668 B1 | 8/1981 |
| EP | 0076897 A1 | 4/1983 |
| EP | 0149997 A2 | 7/1985 |
| EP | 0194257 A1 | 9/1986 |
| EP | 0371285 A2 | 6/1990 |
| EP | 0418464 A2 | 3/1991 |
| EP | 0430559 | 6/1991 |
| EP | 0430566 | 6/1991 |
| EP | 0430559 A2 | 12/1991 |
| EP | 0520231 A2 | 12/1991 |
| EP | 0503767 | 9/1992 |
| EP | 0503794 A1 | 9/1992 |
| EP | 0430559 B1 | 3/1995 |
| EP | 0703735 A1 | 4/1996 |
| EP | 0354661 B1 | 4/1997 |
| EP | 540775 B1 | 7/1997 |
| EP | 0824927 A2 | 2/1998 |
| EP | 0857431 | 8/1998 |
| EP | 653218 B1 | 9/1998 |
| EP | 1064083 A2 | 1/2001 |
| EP | 1064101 A2 | 1/2001 |
| EP | 1111191 A2 | 6/2001 |
| EP | 0703735 | 7/2001 |
| EP | 1128741 A1 | 9/2001 |
| EP | 1128742 A1 | 9/2001 |
| EP | 1148905 A2 | 10/2001 |
| EP | 1203189 A1 | 5/2002 |
| EP | 1217320 A2 | 6/2002 |
| EP | 1298993 A1 | 4/2003 |
| EP | 1299499 A1 | 4/2003 |
| EP | 1299500 A2 | 4/2003 |
| EP | 1301152 A2 | 4/2003 |
| EP | 1349601 A2 | 10/2003 |
| EP | 1357025 A2 | 10/2003 |
| EP | 1390112 A1 | 2/2004 |
| EP | 1409051 A2 | 4/2004 |
| EP | 1439876 A2 | 7/2004 |
| EP | 1454840 | 9/2004 |
| EP | 1454840 A1 | 9/2004 |
| EP | 1490452 A2 | 12/2004 |
| EP | 1506792 A2 | 2/2005 |
| EP | 1609376 A1 | 12/2005 |
| EP | 1625334 A2 | 2/2006 |
| EP | 1625335 A2 | 2/2006 |
| EP | 1625336 A2 | 2/2006 |
| EP | 1454840 | 9/2006 |
| EP | 1536703 B1 | 9/2006 |
| EP | 1702639 A2 | 9/2006 |
| EP | 1749548 A1 | 2/2007 |
| EP | 1867357 A1 | 12/2007 |
| EP | 1891867 A2 | 2/2008 |
| EP | 1940254 A2 | 7/2008 |
| EP | 1996880 A2 | 12/2008 |
| EP | 2044967 A1 | 4/2009 |
| EP | 1357025 | 7/2009 |
| EP | 2277398 A1 | 7/2009 |
| EP | 2083642 A1 | 8/2009 |
| EP | 2110034 | 10/2009 |
| EP | 2138058 A1 | 12/2009 |
| EP | 2138059 A1 | 12/2009 |
| EP | 2179229 A2 | 4/2010 |
| EP | 2191735 A1 | 6/2010 |
| EP | 2227973 A1 | 9/2010 |
| EP | 2234508 A2 | 10/2010 |
| EP | 2241203 A2 | 10/2010 |
| EP | 2138057 B1 | 11/2010 |
| EP | 2246086 A2 | 11/2010 |
| EP | 2249669 A1 | 11/2010 |
| EP | 2253541 A1 | 11/2010 |
| EP | 2257195 A1 | 12/2010 |
| EP | 2303043 A2 | 4/2011 |
| EP | 2316286 | 5/2011 |
| EP | 2327318 A1 | 6/2011 |
| EP | 2368449 A1 | 9/2011 |
| EP | 2003997 B1 | 10/2011 |
| EP | 2408494 A1 | 1/2012 |
| EP | 2444112 | 4/2012 |
| EP | 2253541 | 5/2012 |
| EP | 2472185 A1 | 7/2012 |
| EP | 2523752 A1 | 11/2012 |
| EP | 2542131 A2 | 1/2013 |
| EP | 2760303 A2 | 8/2014 |
| EP | 2907397 A1 | 8/2015 |
| EP | 2996504 A1 | 3/2016 |
| ES | 262308 U | 6/1982 |
| FR | 718708 | 1/1932 |
| FR | 1418189 A | 11/1965 |
| FR | 2573985 A | 6/1986 |
| FR | 2604093 A1 | 3/1988 |
| FR | 2700697 A1 | 7/1994 |
| FR | 2730166 A1 | 8/1996 |
| FR | 2818152 A1 | 6/2002 |
| FR | 2842791 B1 | 1/2005 |
| FR | 2873584 B1 | 11/2006 |
| GB | 347650 | 10/1928 |
| GB | 347650 | 4/1931 |
| GB | 353745 | 7/1931 |
| GB | 910166 A | 11/1962 |
| GB | 922310 B | 3/1963 |
| GB | 958867 A | 5/1964 |
| GB | 1104214 B | 2/1968 |
| GB | 1227333 B | 4/1971 |
| GB | 1379688 B | 1/1975 |

(56) References Cited

FOREIGN PATENT DOCUMENTS

| | | |
|---|---|---|
| GB | 1431334 B | 4/1976 |
| GB | 9521889 | 1/1996 |
| GB | 2294401 A | 5/1996 |
| GB | 2323033 A | 9/1998 |
| GB | 2342874 A | 4/2000 |
| GB | 2388040 A | 11/2003 |
| GB | 2412326 A | 9/2005 |
| GB | 2412876 A | 10/2005 |
| GB | 2448478 A | 10/2008 |
| GB | 2487851 A | 8/2012 |
| GB | 2495923 A | 5/2013 |
| GB | 2504732 | 2/2014 |
| IE | 63083 B1 | 3/1995 |
| IT | 1289590 B1 | 10/1998 |
| JP | 49061986 A | 6/1974 |
| JP | 50096908 A | 8/1975 |
| JP | 55094260 A | 7/1980 |
| JP | 57110260 A | 7/1982 |
| JP | 57177769 A | 11/1982 |
| JP | 63153666 A | 6/1988 |
| JP | 01191674 A | 8/1989 |
| JP | 1166953 U | 11/1989 |
| JP | 02092986 A | 4/1990 |
| JP | H03232481 | 10/1991 |
| JP | H08511175 | 11/1995 |
| JP | H0851175 A | 2/1996 |
| JP | 2519658 B2 | 7/1996 |
| JP | 08228751 A | 9/1996 |
| JP | 3053426 U | 10/1998 |
| JP | H11503912 A | 4/1999 |
| JP | H11507234 A | 6/1999 |
| JP | 11178562 A | 7/1999 |
| JP | 2000051556 A | 2/2000 |
| JP | 3016586 B2 | 3/2000 |
| JP | 2000082576 A | 3/2000 |
| JP | 2000093155 A | 4/2000 |
| JP | 3078033 B2 | 8/2000 |
| JP | 200051556 A | 11/2000 |
| JP | 3118462 B2 | 12/2000 |
| JP | 3118463 B2 | 12/2000 |
| JP | 2002170657 A | 6/2002 |
| JP | 2002253593 A | 9/2002 |
| JP | 2002336290 A | 11/2002 |
| JP | 2003034785 A | 2/2003 |
| JP | 3392138 B2 | 3/2003 |
| JP | 2004055547 A | 2/2004 |
| JP | 2004504580 A | 2/2004 |
| JP | 3588469 | 11/2004 |
| JP | 2005050624 A | 2/2005 |
| JP | 2005516647 A | 6/2005 |
| JP | 2006524494 A | 11/2006 |
| JP | 2007516015 A | 6/2007 |
| JP | 2007522900 A | 8/2007 |
| JP | 2008509907 A | 4/2008 |
| JP | 2008511175 A | 4/2008 |
| JP | 2009509523 A | 3/2009 |
| JP | 2009087703 A | 4/2009 |
| JP | 2010041354 A | 2/2010 |
| JP | 2010526553 A | 8/2010 |
| JP | 2011135901 A | 7/2011 |
| JP | 2012529936 A | 11/2012 |
| JP | 2014526275 A | 10/2014 |
| JP | 2015503336 A | 2/2015 |
| JP | 2015503337 A | 2/2015 |
| JP | 2015060837 A | 3/2015 |
| JP | 2015506170 A | 3/2015 |
| JP | 2015508287 A | 3/2015 |
| JP | 2015509706 A | 4/2015 |
| JP | 2016036222 A | 3/2016 |
| JP | 2016525341 A | 8/2016 |
| JP | 2017515490 A | 6/2017 |
| JP | 2017520234 A | 7/2017 |
| JP | 2017526381 A | 9/2017 |
| JP | 2017533732 A | 11/2017 |
| JP | 2018520664 A | 8/2018 |
| JP | 2021508438 A | 3/2021 |
| KR | 960702734 A | 5/1996 |
| KR | 100385395 B1 | 8/2003 |
| KR | 20040068292 A | 7/2004 |
| KR | 20070096027 A | 10/2007 |
| KR | 100971178 B1 | 7/2010 |
| KR | 20120104533 A | 9/2012 |
| KR | 20140068808 A | 6/2014 |
| KR | 20140123487 A | 10/2014 |
| RU | 2349234 C2 | 3/2009 |
| SE | 7415242 A | 6/1975 |
| SE | 502503 L | 10/2006 |
| TW | 274507 | 4/1996 |
| TW | 201325481 A | 7/2013 |
| WO | WO 8404698 | 12/1984 |
| WO | 86/01730 A1 | 3/1986 |
| WO | WO 9409842 | 5/1994 |
| WO | 95/27411 A1 | 10/1995 |
| WO | WO 9527411 | 10/1995 |
| WO | WO-9639880 A1 | 12/1996 |
| WO | 98/05906 A1 | 2/1998 |
| WO | WO-9823171 A1 | 6/1998 |
| WO | 98/35552 A1 | 8/1998 |
| WO | 99/14402 A1 | 3/1999 |
| WO | 99/47273 A2 | 9/1999 |
| WO | 99/47806 A2 | 9/1999 |
| WO | 90/13326 A1 | 11/1999 |
| WO | 00/28843 A1 | 5/2000 |
| WO | 01/04548 A1 | 1/2001 |
| WO | 01/40717 A1 | 6/2001 |
| WO | 01/63183 A1 | 8/2001 |
| WO | 02/05620 A2 | 1/2002 |
| WO | 02/05640 A1 | 1/2002 |
| WO | 02/06421 A1 | 1/2002 |
| WO | 02/07656 A2 | 1/2002 |
| WO | 02/04262 A2 | 3/2002 |
| WO | 02/051466 A2 | 7/2002 |
| WO | 02/096532 A1 | 12/2002 |
| WO | WO 02098389 | 12/2002 |
| WO | 03/037412 A2 | 5/2003 |
| WO | 03/049792 A1 | 6/2003 |
| WO | 03/083007 A2 | 10/2003 |
| WO | 2004/098324 A2 | 11/2004 |
| WO | 2004/104491 A2 | 12/2004 |
| WO | 2004/104492 A2 | 12/2004 |
| WO | 2004/104493 A2 | 12/2004 |
| WO | 2006/022714 A1 | 3/2006 |
| WO | WO-2007042941 A2 | 4/2007 |
| WO | 2007/054167 A1 | 5/2007 |
| WO | WO-2007051163 A2 | 5/2007 |
| WO | 2007/078273 A1 | 7/2007 |
| WO | 2007/090594 A1 | 8/2007 |
| WO | 2007/098337 A2 | 8/2007 |
| WO | 2007/116915 A1 | 10/2007 |
| WO | 2008/015441 A1 | 2/2008 |
| WO | WO-2008029381 A2 | 3/2008 |
| WO | 2008/051909 A1 | 5/2008 |
| WO | 2008/069883 A1 | 6/2008 |
| WO | 2008/151777 A2 | 12/2008 |
| WO | 2009/006521 A2 | 1/2009 |
| WO | 2009/042955 A2 | 4/2009 |
| WO | 2009/079641 A2 | 6/2009 |
| WO | 2009/092862 A1 | 7/2009 |
| WO | WO 2009092862 | 7/2009 |
| WO | 2009/118085 A1 | 10/2009 |
| WO | 2009/152651 A1 | 12/2009 |
| WO | 2009/155957 A2 | 12/2009 |
| WO | 2009/156181 A2 | 12/2009 |
| WO | 2010/017586 A1 | 2/2010 |
| WO | 2010/047389 A1 | 4/2010 |
| WO | WO-2010041354 A1 | 4/2010 |
| WO | 2010/053467 A1 | 5/2010 |
| WO | 2010/060537 A1 | 6/2010 |
| WO | 2010/107613 A1 | 9/2010 |
| WO | 2011/088132 A1 | 7/2011 |
| WO | 2011/101164 A1 | 8/2011 |
| WO | 2011/109304 A2 | 9/2011 |
| WO | 2011/117580 A2 | 9/2011 |
| WO | 2012/054973 A1 | 5/2012 |

(56) References Cited

FOREIGN PATENT DOCUMENTS

| WO | 2012/078865 A2 | 6/2012 |
|---|---|---|
| WO | WO 2012/072790 | 6/2012 |
| WO | WO-2012072770 A1 | 6/2012 |
| WO | 2012/100430 A1 | 8/2012 |
| WO | WO 2013034455 | 3/2013 |
| WO | WO 2013076098 | 5/2013 |
| WO | WO 2013/098405 | 7/2013 |
| WO | WO 2013/098409 | 7/2013 |
| WO | WO 2013/098410 | 7/2013 |
| WO | WO2013/102609 | 7/2013 |
| WO | WO 2013098395 | 7/2013 |
| WO | WO 2014048745 | 4/2014 |
| WO | WO2013/034458 | 6/2014 |
| WO | WO-2015051646 A1 | 4/2015 |
| WO | WO-2015068936 A1 | 5/2015 |
| WO | WO-2015082648 A1 | 6/2015 |
| WO | WO-2015131058 A1 | 9/2015 |
| WO | WO-2015177044 A1 | 11/2015 |
| WO | WO-2015177045 A1 | 11/2015 |
| WO | WO-2015177255 A1 | 11/2015 |
| WO | WO-2015177263 A1 | 11/2015 |
| WO | WO-2015177264 A1 | 11/2015 |
| WO | WO-2015177265 A1 | 11/2015 |
| WO | WO-2015177294 A1 | 11/2015 |
| WO | WO-2015198015 A1 | 12/2015 |
| WO | WO-2016014652 A1 | 1/2016 |
| WO | WO-2016156500 A1 | 10/2016 |
| WO | WO-2016184928 A1 | 11/2016 |
| WO | WO-2016184929 A1 | 11/2016 |
| WO | WO-2016184930 A1 | 11/2016 |
| WO | WO-2016200815 A2 | 12/2016 |
| WO | WO-2017001819 A1 | 1/2017 |
| WO | WO-2017005705 A1 | 1/2017 |
| WO | WO-2017029268 A1 | 2/2017 |
| WO | WO-2017029269 A1 | 2/2017 |
| WO | WO-2017029272 A1 | 2/2017 |
| WO | WO-2017036950 A2 | 3/2017 |
| WO | WO-2017036955 A2 | 3/2017 |
| WO | WO-2017036959 A1 | 3/2017 |
| WO | WO-2017068094 A1 | 4/2017 |
| WO | WO-2017068098 A1 | 4/2017 |
| WO | WO-2017068099 A1 | 4/2017 |
| WO | WO-2017207581 A1 | 12/2017 |
| WO | WO-2018002083 A1 | 1/2018 |
| WO | WO-2018178095 A1 | 10/2018 |

OTHER PUBLICATIONS jrank.org, Heat Capacity—Heat Capacity and Calorimetry, Heat Capacity and the Law of Conservation of Energy—Significance of the high heat capacity of water, Accessed Jun. 15, 2017, <science.jrank.org>.*
Chaplin, Martin, "Hydrocolloids and gums", Established in 2001, <wwwl.lsbu.ac.uk/water/hydrocolloids_gums.html>. (Year: 2001).*
Rasidek, Noor Azwani Mohd, "Effect of Temperature on Rheology Behaviour of Banana Peel Pectin Extracted Using Hot Compressed Water," Published Apr. 1, 2018, Accessed Dec. 4, 2018 Jurnal Teknologi (Sciences & Engineering), 80:3, p. 97-103 (Year: 2018).*
The Engineering Toolbox, "Specific Heats for Metals," Published 2003, Accessed Dec. 4, 2018 (Year: 2003).*
Ineos, "Typical Engineering Properties of High Density Polyethylene," Accessed Dec. 4, 2018. (Year: 2018).*
UKIPO Search Report, dated Jan. 17, 2013, for UK Patent Application No. GB1216621.1, filed Sep. 18, 2012.
International Search Report and Written Opinion, dated Jun. 30, 2014, for International Patent Application No. PCT/GB2013/052433, filed Sep. 18, 2013.
International Preliminary Report on Patentability, dated Mar. 24, 2015, for International Patent Application No. PCT/GB2013/052433, filed Sep. 18, 2013.
International Search Report and Written Opinion, dated Dec. 9, 2013, for International Patent Application No. PCT/EP2013/068797, filed Sep. 11, 2013.
International Preliminary Report on Patentability, dated Mar. 31, 2015, for International Patent Application No. PCT/EP2013/068797, filed Sep. 11, 2013.
Russian Office Action, Application No. 2015106592/12, dated Sep. 13, 2017, 6 pages.
Application and File History for U.S. Appl. No. 14/927,529, filed Oct. 30, 2015, inventors Kaufman et al.
Application and File History for U.S. Appl. No. 14/840,854, filed Aug. 31, 2015, inventors Blandino et al.
Application and File History for U.S. Appl. No. 14/927,532, filed Oct. 30, 2015, inventors Blandino et al.
Application and File History for U.S. Appl. No. 14/840,972, filed Aug. 31, 2015, inventors Wilke et al.
Application and File History for U.S. Appl. No. 14/840,652, filed Aug. 31, 2015, inventors Blandino et al.
Application and File History for U.S. Appl. No. 14/840,703, filed Aug. 31, 2015, inventors Wilke et al.
Application and File History for U.S. Appl. No. 14/840,731, filed Aug. 31, 2015, inventors Blandino et al.
Application and File History for U.S. Appl. No. 14/840,751, filed Aug. 31, 2015, inventors Blandino et al.
Iorga, Alexandru et al., "Low Curie Temperature in Fe—Cr—Ni—Mn Alloys", U.P.B. Sci.Bull., Series B, vol. 73, Iss.4, 2011. 195-202. 8 pages.
Todaka et al., "Low Curie Temperature Material for Induction Heating Self-Temperature Controlling System", Journal of Magnetism and Magnetic Materials 320 (2008). 6 pages. e702-e707.
NeoMax MS-135, from NeoMax Materials Co., Ltd., described at the following URL: http://www.neomax-materials.co.jp/eng/pr0510.htm As accessed on Oct. 30, 2015.
Chinese First Office Action for Chinese Application No. 201380021387.2 dated Dec. 3, 2015.
Chinese Second Office Action for Chinese Application No. 201380048636.7 dated Jan. 16, 2017.
Chinese First Office Action for Chinese Application No. 201380048636.7 dated May 5, 2016.
Japanese Notification of Reasons for Refusal for Japanese Application No. 2015531544 dated Feb. 1, 2016.
Japanese Office Action, Application No. 2017-075527, dated Mar. 13, 2018, 5 pages (10 pages with translation).
Japanese Office Action, Application No. 2017075527, dated Dec. 25, 2018, 16 pages. (with translation).
Korean Office Action, Application No. 10-2018-7006009, dated Jan. 31, 2019, 17 pages, 2019.
International Search Report and Written Opinion, Application No. PCT/EP2016/070176, dated Apr. 19, 2017, 21 pages.
Canadian Office Action, Application No. 2,995,315, dated Feb. 19, 2019, 4 pages.
Chinese Office Action, Application No. 201680049679.0, dated Nov. 4, 2019, 12 pages.
CN203762288U, "Atomization Device Applicable to Solid Tobacco Materials and Electronic Cigarette," retrieved from Google Patents https://patents.google.com/patent/CN203762288U/en on Jan. 12, 2018, 10 pages.
English Translation of Chinese First Office Action, Application No. 2016800498584, dated Nov. 1, 2019, 6 pages.
English translation of CN101390659 dated Aug. 3, 2017, 8 pages.
English Translation of Japanese Office Action, Application No. 2018-521547, dated Jun. 25, 2019, 4 Pages.
English Translation of Japanese Office Action, Application No. 2018-506565, dated Mar. 19, 2019, 4 pages.
English Translation of Korean Office Action, Application No. 10-2018-7006070, dated Feb. 7, 2019, 9 pages.
Gaohe Q.,"Chinese Scientific Information", May 15, 2010, vol. 10, pp. 132-133.
International Preliminary Report on Patentability for Application No. PCT/EP2016/070176, dated Mar. 15, 2018, 12 pages.
International Preliminary Report on Patentability for Application No. PCT/EP2016/070178, dated Mar. 15, 2018, 8 pages.
International Preliminary Report on Patentability for Application No. PCT/EP2016/070182, dated Mar. 15, 2018, 8 pages.
International Preliminary Report on Patentability for Application No. PCT/EP2016/070185, dated Mar. 15, 2018, 11 pages.

(56) References Cited

OTHER PUBLICATIONS

International Preliminary Report on Patentability for Application No. PCT/EP2016/070188, dated Mar. 15, 2018, 8 pages.
International Preliminary Report on Patentability for Application No. PCT/EP2016/070191, dated Mar. 15, 2018, 8 pages.
International Preliminary Report on Patentability for Application No. PCT/EP2016/075734, dated May 11, 2018, 7 pages.
International Preliminary Report on Patentability for Application No. PCT/EP2016/075739, dated Jan. 16, 2018, 7 pages.
International Search Report and Written Opinion for Application No. PCT/EP2016/070178, dated Dec. 14, 2016, 10 pages.
International Search Report and Written Opinion for Application No. PCT/EP2016/070182, dated Dec. 12, 2016, 11 pages.
International Search Report and Written Opinion for Application No. PCT/EP2016/070185, dated Apr. 4, 2017, 16 pages.
International Search Report and Written Opinion for Application No. PCT/EP2016/070188, dated Dec. 13, 2016, 10 pages.
International Search Report and Written Opinion for Application No. PCT/EP2016/070191, dated Dec. 13, 2016, 10 pages.
International Search Report and Written Opinion for Application No. PCT/EP2016/075734, dated Apr. 6, 2017, 12 pages.
International Search Report and Written Opinion for Application No. PCT/EP2016/075739, dated Feb. 24, 2017, 10 pages.
Japanese Office Action, Application No. 2018-506575, dated Nov. 12, 2019, 8 pages.
Japanese Office Action, Application No. 2018-506565, dated Nov. 5, 2019, 7 pages.
Japanese Office Action, Application No. 2018-507624, dated Oct. 29, 2019, 14 pages.
Office Action dated Feb. 13, 2019 for Japanese Application No. 2018-507624, 32 pages.
Office Action dated Feb. 14, 2019 for Canadian Application No. 2996835, 3 pages.
Office Action dated Feb. 8, 2019 for Korean Application No. 10-2018-7006077, 8 pages (15 pages with translation).
Korean Office Action, Application No. 10-2018-7006009, dated Aug. 29, 2019, 9 pages.
Japanese Office Action, Application No. 2018-506381, dated Mar. 26, 2019, 11 pages.
Chinese Office Action, Application No. 2016800498156, dated Oct. 21, 2019, 20 pages.
Japanese Office Action, Application No. 2018-506553, dated Mar. 19, 2019, 8 pages.
Japanese Office Action, Application No. 2018-506553, dated Nov. 5, 2019, 12 pages.
Taiwanese Office Action, Application No. 105127626, dated May 3, 2020, 10 pages.
English Translation of Chinese Office Action, Application No. 2016800498156, dated May 6, 2020, 7 pages.
European Notice of Opposition, Application No. 13759537.7, dated Jan. 23, 2020, 83 pages.
Polyetheretherketone, Online Catalog Source, available at www.goodfellow.com/a/Polyethertherketone.html, 4 pages, retrieved on Jan. 17, 2020.
Application and File History for U.S. Appl. No. 14/927,537, filed Oct. 30, 2015, inventors Kaufman et al.
Application and File History for U.S. Appl. No. 14/927,539, filed Oct. 30, 2015, inventors Blandino et al.
Application and File History for U.S. Appl. No. 14/927,551, filed Oct. 30, 2015, inventors Blandino et al.
Application and File History for U.S. Appl. No. 14/927,556, filed Oct. 30, 2015, inventors Blandino et al., 60 pages.
Application and File History for U.S. Appl. No. 15/754,801, filed Feb. 23, 2018, inventors Blandino et al.
Application and File History for U.S. Appl. No. 15/754,809, filed Feb. 23, 2018, Inventors Wilke et al.
Application and File History for U.S. Appl. No. 15/754,812, filed Feb. 23, 2018, Inventors Blandino et al.
Application and File History for U.S. Appl. No. 15/754,818, filed Feb. 23, 2018, Inventors Blandino et al.
Application and File History for U.S. Appl. No. 15/754,823, filed Feb. 23, 2018, Inventors Blandino et al.
Application and File History for U.S. Appl. No. 15/754,837, filed Feb. 23, 2018, Inventors Wilke et al.
Application and File History for U.S. Appl. No. 15/772,382, filed Apr. 30, 2018, Inventors Kaufman Wilke et al.
Application and File History for U.S. Appl. No. 15/772,386, filed Apr. 30, 2018, Inventors Blandino et al.
CN203762288, Machine Translation, retrieved Online from Espacenet on Aug. 13, 2020, (http://worldwide.espacenet.com), 5 pages.
European Extended Search Report for Application No. 19216472.1 dated Apr. 22, 2020, 13 Pages.
Extended European Search Report for Application No. 19164405.3 dated Aug. 28, 2019, 6 pages.
Extended European Search Report for Application No. 19165045.6 dated Sep. 6, 2019, 7 Pages.
Extended European Search Report for Application No. 20179569.7 dated Oct. 2, 2020, 10 pages.
Office Action dated Oct. 18, 2019 for Chinese Application No. 201680049874.3, 18 pages.
Office Action dated Aug. 5, 2020 for Chinese Application No. 201680049874.3, 6 pages.
Office Action for Chinese Application No. 20168049858 dated Jul. 3, 2020, 35 pages.
Office Action dated Sep. 1, 2020 for Japanese Application No. 2018-506381, 25 pages.
Office Action dated Sep. 12, 2019 for Chilean Application No. 201800521, 8 pages.
Office Action dated Sep. 15, 2020 for Japanese Application No. 2019-118784, 14 pages.
Office Action dated Sep. 17, 2020 for Canadian Application No. 2996342, 4 pages.
Office Action dated Dec. 19, 2019 for Taiwan Application No. 105127627, 14 pages.
Office Action dated Mar. 19, 2019 for Japanese Application No. 2018-506575, 10 pages.
Office Action dated Jun. 25, 2019 for Japanese Application No. 2018-519865, 3 pages.
Office Action dated Apr. 27, 2020 for the Brazilian Application No. 112017028539.8, 5 pages.
Office Action dated Mar. 28, 2019 for Canadian Application No. 3003514, 6 pages.
Office Action dated Sep. 29, 2020 for Japanese Application No. 2018-506563, 5 pages.
Office Action dated Dec. 3, 2019 for Japanese Application No. 2018-521547, 4 pages.
Office Action dated Dec. 3, 2019 for Japanese Application No. 2018-506381, 8 pages.
Office Action dated May 7, 2019 for Japanese Application No. 2018-506563, 4 pages.
Office action dated Sep. 8, 2020 for Japanese Application No. 2018-507624, 7 pages.
Office Action dated Jun. 9, 2020 for Chinese Application No. 201680061969.7, 15 pages.
Shuisheng X., et al., "Semisolid processing technology," Jinshu Bangutai Jiagong Jishu, 2012, ISBN 978-7-5024-5935-2, 10 pages.
Extended European Search Report for Application No. 20205043.1, dated May 4, 2021, 10 pages.
Extended European Search Report For Application No. 20205544.8 dated Jun. 14, 2021, 9 pages.
Extended European Search Report for Application No. EP20205075.3, dated Jan. 27, 2021, 11 pages.
International Search Report and Written Opinion for Application No. PCT/EP2016/085686, dated May 9, 2019, 16 pages.
Jinshu Bangutai Jiagong Jishu, Metallurgical Industry Press, 10 pages, dated Jun. 30, 2012.
Notification of Reasons for Refusal dated May 18, 2021 for Japanese Application No. 2020126181, 8 pages.
Office Action dated Feb. 15, 2021 for Ukraine Application No. 201801751, 4 pages.
Office Action dated Feb. 16, 2021 for Ukraine Application No. 201801846, 3 pages.

(56) References Cited

OTHER PUBLICATIONS

Office Action dated Jan. 28, 2021 for Chinese Application No. 201680049874.3, 6 pages.
Office Action For Chinese Application No. 201680049479.5, dated Feb. 4, 2021, 8 pages.
Office Action For Japanese Application No. 2018-506381, dated Apr. 13, 2021, 5 pages.
Office Action for Malaysian Application No. PI2018700428, dated Mar. 1, 2021, 3 pages.
Office Action dated Jun. 19, 2020 for Canadian Application No. 2995315, 4 pages.
Partial European Search Report for Application No. 20205057.1, dated Apr. 29, 2021, 16 pages.
Office Action dated Sep. 17, 2020 for Canadian Application No. 2995315, 4 pages.
Office Action For Russian Application No. 2020121132, dated Aug. 6, 2021, 11 pages.
Office Action For Russian Application No. 2020135756, dated Jun. 30, 2021, 9 pages.
Office Action dated Jun. 8, 2021 for Japanese Application No. 2020-526233, 22 pages.

* cited by examiner

HEATING SMOKEABLE MATERIAL

CLAIM FOR PRIORITY

This application is the National Stage of International Application No. PCT/EP2013/068797, filed Sep. 11, 2013, which in turn claims priority to and benefit of United Kingdom Patent Application No. GB1217067.6, filed Sep. 25, 2012. The entire contents of the aforementioned applications are herein expressly incorporated by reference.

FIELD

The invention relates to heating smokable material in order to volatilize components of the smokable material.

BACKGROUND

Smoking articles such as cigarettes and cigars burn tobacco during use to create tobacco smoke. Attempts have been made to provide alternatives to these smoking articles by creating products which release compounds without creating tobacco smoke. Examples of such products are so-called heat-not-burn products which release compounds by heating, but not burning, tobacco.

SUMMARY

According to the invention, there is provided an apparatus configured to volatilize components of smokable material for inhalation, comprising:
 a smokable material heating chamber; and
 a heating material which is configured to be heated by the presence of a varying magnetic field, wherein the heating material is arranged to transfer heat energy to smokable material in the heating chamber to volatilize said components.

The heating material may be comprised in a heating member.

The heating member may comprise a base material in thermal contact with the heating material, the base material being configured to retain heat energy received from the heating material and to transfer the heat energy to smokable material in the heating chamber to volatilize said components.

The base material may be configured to transfer said heat energy to said smokable material over an extended period so as to raise and maintain a temperature of said smokable material at a volatilizing temperature for said extended period without simultaneous heating of the heating material by the varying magnetic field.

The heating material may comprise a plurality of pieces of heating material dispersed in the heating member with the base material.

The heating member may comprise an elongate member located adjacent the smokable material heating chamber.

The heating chamber may be located co-axially around the heating member.

The heating material may be located inside the smokable material heating chamber with the smokable material.

The heating material may comprise a plurality of pieces of heating material dispersed within the smokable material.

The heating material may comprise an electrically conductive material.

The heating material may be susceptible to eddy currents induced by the varying magnetic field in the material, the eddy currents causing the heating material to be resistively heated.

The apparatus may comprise a housing in which the heating chamber and heating material are contained and a varying magnetic field generator arranged to receive the housing during heating of the heating material.

The field generator may be arranged to releasably dock with the housing, thereby maintaining a stable position of the housing relative to the generator during heating.

The apparatus may comprise a mouthpiece in fluid communication with the heating chamber in order to allow volatilized components of the smokable material to be drawn through the mouthpiece by a user.

The heating material may be configured to heat the smokable material to a volatilizing temperature of between approximately 50° C. and 250° C. to volatilize said components.

According to the invention, there is provided a method of heating smokable material to volatilize components of the smokable material for inhalation, comprising:
 generating a varying magnetic field;
 using the varying magnetic field to induce an electrical current in a heating material and thereby heating the heating material;
 transferring thermal energy from the heating material to the smokable material to heat the smokable material to a volatilizing temperature and thereby volatilize components of the smokable material.

According to the invention, there is provided a method of heating smokable material to volatilize components of the smokable material for inhalation, comprising:
 inserting a housing containing heating material and smokable material into a device configured to generate a varying magnetic field;
 generating the varying magnetic field in the device and thereby heating the heating material by causing an electrical current to be induced in the heating material;
 transferring thermal energy from the heating material to the smokable material to heat the smokable material to a volatilizing temperature and thereby volatilize components of the smokable material.

There may also be provided an apparatus for performing the method, comprising:
 a housing containing smokable material and a heating material; and
 a device configured to generate a varying magnetic field.

For the purposes of example only, embodiments of the invention are described below with reference to the accompanying drawings, in which:

DETAILED DESCRIPTION

Figure 1:
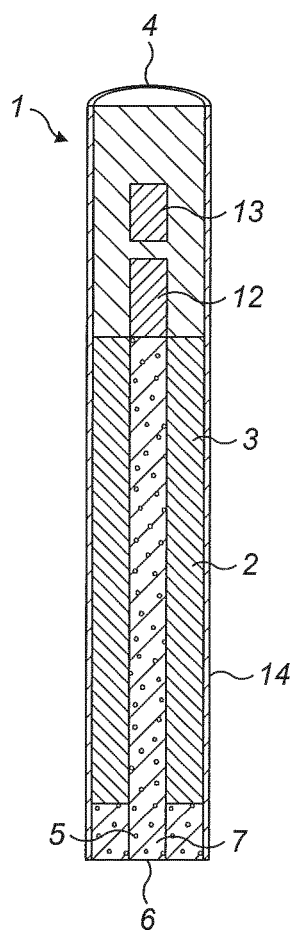
FIG. 1 is a partially cut away illustration of an apparatus for providing volatilized components of heated smokable material for inhalation by a user, in which a heating member comprising an electrically conductive heating material is located adjacent a smokable material heating chamber.

As used herein, the term 'smokable material' includes any material that provides volatilized components upon heating and includes any tobacco-containing material and may, for example, include one or more of tobacco, tobacco derivatives, expanded tobacco, reconstituted tobacco or tobacco substitutes.

An apparatus 1 for providing volatilized components of smokable material 2 for inhalation comprises a smokable material heating chamber 3 and a mouthpiece 4 which is fluidly connected with the heating chamber 3. The mouthpiece 4 may comprise a filter material such as cellulose acetate tow, which may be provided in the form of a wrapped plug. A user of the apparatus 1 can inhale the volatilized components from the mouthpiece 4 when the smokable material 2 is heated inside the heating chamber 3 to a temperature which is sufficient to volatilize the smokable material components.

As described more fully below, the smokable material 2 is heated by thermal transfer from a heating material 5 located in the proximity of the smokable material 2. The heating material 5 itself is resistively heated in an electromagnetic induction heating process.

More particularly, the heating material 5 comprises electrically conductive material of finite electrical resistance in which induced eddy currents cause resistive heating of the material 5 when the heating material 5 is placed in a varying magnetic field. An example of a suitable heating material 5 is Iron, although other electrically conductive materials could alternatively be used such as another electrically conductive metal or alloy. The heating material 5 is heated by the effects of electromagnetic induction to a temperature which is sufficient to volatilize components of the smokable material 2 in the heating chamber 3, such as nicotine and aromatic compounds, without burning the smokable material 2.

The heating material 5 may be located either inside the heating chamber 3 or in its close proximity. As explained below, an example is for the heating material 5 to be located either directly adjacent the smokable material 2 or in a heating member 6 which is located directly adjacent the smokable material 2. The location of the heating material 5 is such that effective thermal transfer takes place between the heated heating material 5 and the smokable material 2 inside the heating chamber 3, thereby causing the smokable material 2 to be heated to a temperature which is sufficient to volatilize components of the smokable material 2 for inhalation through the mouthpiece 4.

As briefly referred to above, the heating material 5 may be comprised in a heating member 6 which is configured to transfer thermal energy from the heating material to smokable material 2 in the heating chamber 3. In addition to the heating material 5, the heating member 6 may comprise a base material 7 which is heat retentive and acts to release heat energy received from the heating material 5 over a relatively long period and thereby maintain the smokable material 2 at a volatilizing temperature for the duration of that period. An example is between approximately three and ten minutes, as discussed further below. The base material 7 may be an electrical insulator which, unlike the heating material 5, is not itself susceptible to induction of electrical eddy currents when placed in a varying magnetic field.

The base material 7 is in thermal contact with the heating material 5 so that, when the heating material 5 is heated by electromagnetic induction, thermal energy from the heating material 5 conducts into the base material 7 and causes it to heat up to the temperature of the heating material 5. The heat stored in the base material 7 then dissipates into the heating chamber 3 over an extended period so as to continuously heat the smokable material 2 therein and cause components of the smokable material 2 to be continuously volatilized for inhalation through the mouthpiece 4.

An example of a suitable base material 7 is a material with a high specific heat capacity, which may be higher than that of the heating material 5. An example is a specific heat capacity in the range of between approximately 1000 and 3500 J/kg.K, although other values may also be suitable. The material 7 may be a polymer, although other materials 7 could alternatively be used. An example of a suitable material 7 is HDPE or a Polycarbonate. As explained briefly above, the base material 7 is configured to store the heat energy received from the heating material 5 and to gradually dissipate the thermal energy from the heating material 5 over the extended period referred to above so as to heat the smokable material 2 to within a desired volatilizing temperature range and to maintain the temperature of the smokable material 2 in the desired volatilizing temperature range until the extended period has elapsed. An example of a temperature range in which components of smokable material such as tobacco are volatilized is between approximately 50° C. and approximately 250° C., such as between approximately 50° C. and 150° C., between approximately 50° C. and 120° C., between approximately 50° C. and 100° C., between approximately 50° C. and 80° C. or between approximately 60° C. and 70° C. Other ranges may also be suitable. The extended period may be approximately the same length as the period taken to smoke a conventional cigarette. An example period is between approximately four and eight minutes, such as approximately seven minutes.

The heating material 5 and base material 7 (if used) may optionally be placed in the varying magnetic field in between puffs in order to re-heat the heating material 5 before each puff.

The heating member 6 may extend along a longitudinal axis of the apparatus 1. The heating chamber 3 may also extend along a longitudinal axis of the apparatus 1 and may be located adjacent to the heating member 6. For example, the heating member 6 shown in FIG. 1 extends substantially along the central longitudinal axis of the apparatus 1 and the heating chamber 3 is located around its longitudinal surface. If the heating member 6 is substantially cylindrical, as shown in FIG. 1, then the longitudinal surface around which the heating chamber 3 extends is a circumferential surface of the heating member 6. In this type of configuration, the heating chamber 3 may comprise a co-axial layer around the heating member 6. This provides an annular space around the heating member 6 into which the smokable material 2 can be inserted for heating, as described below.

An alternative arrangement is for the positions of the heating chamber 3 and heating member 6 to be reversed, so that the heating chamber 3 is located along the central longitudinal axis of the apparatus 1 and the heating member 6 is located annularly around it as a co-axial layer.

As illustrated in FIG. 1, the heating material 5 may comprise a plurality of separate pieces of heating material 5 which are distributed throughout the base material 7 in the heating member 6. The substantially even distribution of the heating material 5 through the base material 7 provides even heating of the base material 7 when the heating material 5 is heated and therefore also provides even heating of the smokable material 2 in the heating chamber 3. However, it will be appreciated that the use of a plurality of separate pieces of heating material 5 is not a requirement of the invention and that alternative configurations are equally possible for providing even heating of the base material 7 and/or smokable material 2.

Figure 3:
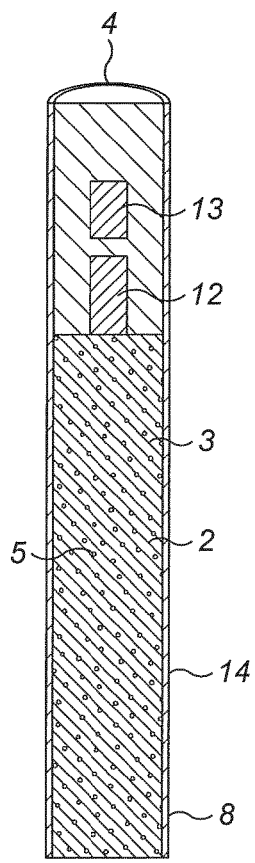
FIG. 3 is a cross-sectional illustration of an apparatus for providing volatilized components of heated smokable material for inhalation by a user, in which an electrically conductive heating material is located with smokable material in a heating chamber.

Another alternative arrangement is illustrated in FIG. 3, in which the heating material 5 resides within the smokable material 2 itself rather than within the heating member 6 described previously. As can be seen from FIG. 3, a plurality of pieces of the heating material 5 may be substantially evenly distributed throughout the smokable material 2 so as to provide even heating of the smokable material 2 across the chamber 3 when the heating material 5 is heated up by induced electrical currents. These individual pieces of heating material 5 may be surrounded by base material 7 so that the heating chamber 3 contains a plurality of heating members 6, each comprising heating material 5 and base material 7, distributed throughout the chamber 3. For example, the heating members 6 may be approximately spherical within an inner core of heating material 5 and an outer layer of base material 7.

The depth or otherwise transverse dimension of the heating chamber 3 may be between approximately 2 mm and 10 mm, such as approximately 5 mm. This may or may not include the base material 5 if it is arranged as a co-axial core in the heating chamber, as discussed above. The length of the heating chamber 3 may be approximately equal to the length of a smokable material rod in a conventional cigarette. An example of a suitable length is between approximately 55 mm and 60 mm although other lengths could alternatively be used.

Figure 2:
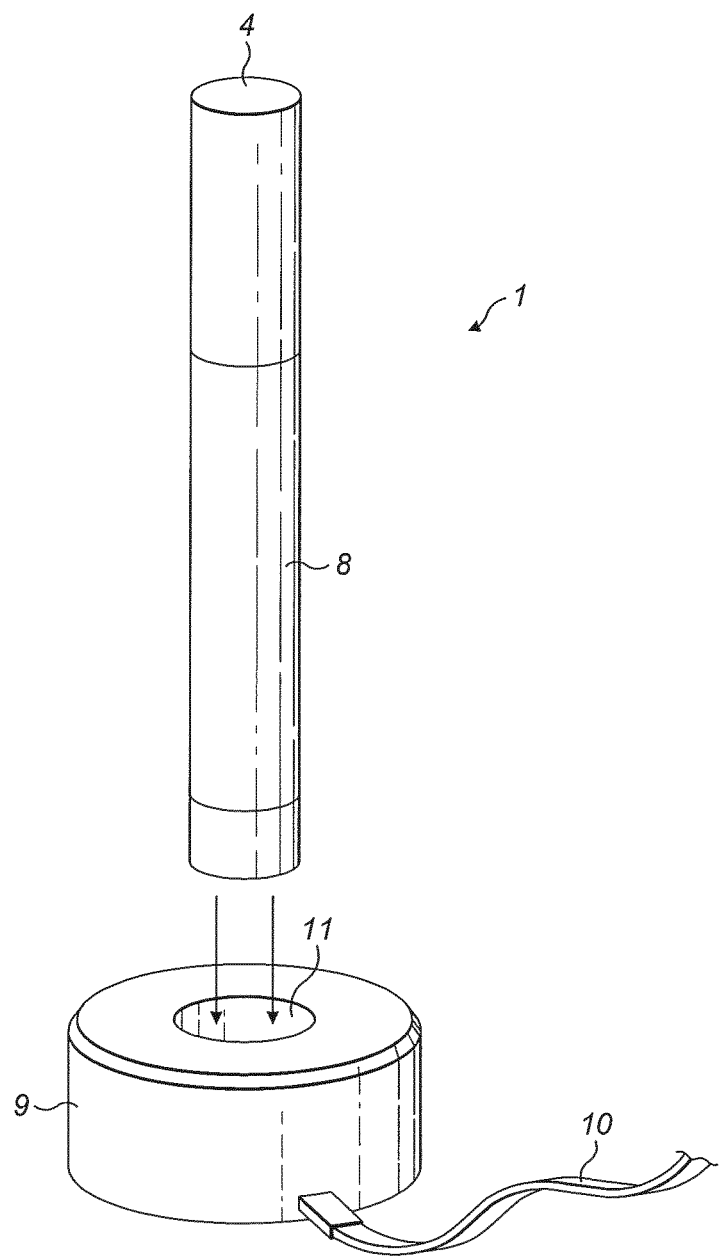
FIG. 2 is a perspective illustration of an apparatus for providing volatilized components of heated smokable material for inhalation by a user, in which a housing of the apparatus is docked in a magnetic field generator for inducing eddy currents in a heating material.

A housing 8 may contain components of the apparatus 1 such as the heating chamber 3, mouthpiece 4, heating material 5 and base material 7. In FIGS. 1 and 2, the housing 8 is illustrated as being elongate with the mouthpiece 4 located at a first of its ends and the heating member 6 and heating chamber 3 extending along a longitudinal axis of the housing 8 through the interior region of the housing 8 from the housing's opposite second end. The housing 8 may, for example, be substantially tubular in shape, such as a pipe, with dimensions similar to those of a cigarette, cigar or cigarillo. The housing 8 may be formed of plastics, such as a suitable polymer material which is comfortable for a user of the apparatus 1 to hold during inhalation and general use.

Figure 4:
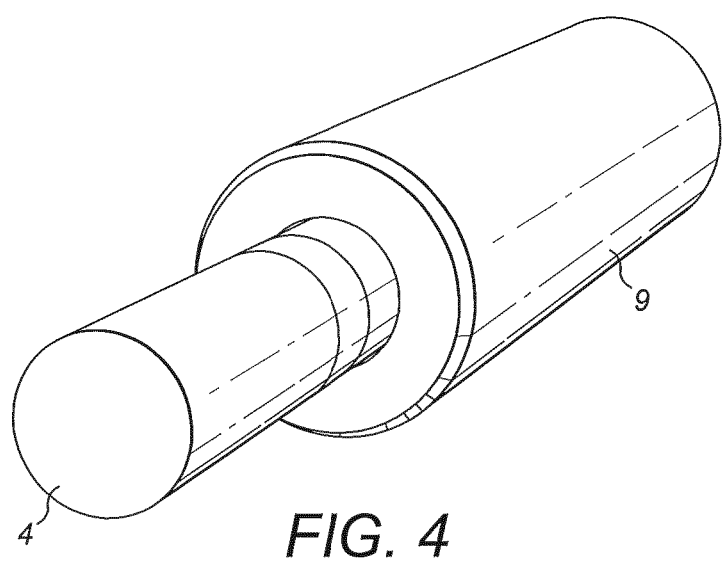
FIG. 4 is a perspective illustration of an apparatus for providing volatilized components of heated smokable material for inhalation by a user, in which a housing of the apparatus is docked in a magnetic field generator for inducing eddy currents in a heating material.

The varying magnetic field which causes currents to be induced in the heating material 5 may be generated by a magnetic field generator 9, examples of which are illustrated in FIGS. 2 and 4. The magnetic field generator 9 may comprise a power source 10, such as a suitable cell or battery, which provides electrical power for generating the varying magnetic field. The field generator 9 may alternatively be configured to receive electrical power from an external power supply, such as a mains power supply, personal computer or other external power source.

The field generator 9 may comprise an electrical coil in which a varying electrical current, such as an alternating current, is caused to flow to create a varying electromagnetic field such as a varying RF field in the vicinity of the generator 9. The varying magnetic flux created by the field generator 9 causes eddy currents to be induced in the heating material 5 when the heating material 5 is located in the vicinity of the generator 9. As described previously, these eddy currents in turn cause resistive heating to occur in the heating material 5 and can thus cause an increase in the temperature of the heating material 5.

The magnetic field generator 9 may be separate from the housing 8 in which the heating member 6, heating chamber 3 and smokable material 2 are located. In this case, the field generator 9 may be configured to structurally engage with the heating chamber housing 8 during heating of the heating material 5 so that the housing 8 and the apparatus components therein are held in a stable arrangement relative to the magnetic field source 9. For example, referring to FIGS. 2 and 4, the magnetic field generator 9 may comprise a recess 11 into which the housing 8 can be inserted. An interior shape of the recess 11 may substantially match an exterior shape of an end region of the housing 8 so that the end region of the housing 8 can be docked and therefore physically secured inside the field generator 9.

The action of docking the housing 8 in the field generator 9 may trigger the generator 9 to generate the varying magnetic field and therefore begin the process of heating the heating material 5 to obtain volatilized smokable material components.

The field generator 9 may be located within a distance of approximately 5 mm to 100 mm of the heating material 5 when the generator 9 is in use, for example when the housing 8 is docked in the generator 9. This range is an example and other suitable distances outside of the range could alternatively be used.

As previously described, heat from the heating material 5 dissipates into the smokable material 2 in the heating chamber 3 and causes components of the smokable material 2 to be volatilized when the smokable material 2 reaches a volatilizing temperature. Optionally, the apparatus 1 may comprise a temperature sensor 12, for example comprising a thermocouple, which is configured to detect when the heating material 5, base material 7 and/or smokable material 2 in the heating chamber 3 has reached a predetermined volatilizing temperature. The temperature sensor 12 may comprise or communicate with an alarm, indicator light or some other suitable alerting unit, which is configured to alert a user that the volatilizing temperature has been reached and thus volatilized components of the smokable material 2 are available for inhalation.

Additionally or alternatively, the apparatus 1 may comprise a timer 13 which is configured to measure the length of time that the heating material 5 has been exposed to the varying magnetic field and to cause the user to be alerted when a predetermined heating time, which is known to correspond to the volatilizing temperature being reached in the heating chamber 3, has elapsed. The timer 13 may be activated automatically by the apparatus 1 upon detecting or otherwise receiving information that the housing 8 has been docked in the magnetic field generator 9.

Once the heating material 5 has been heated to the predetermined volatilizing temperature, the housing 8 can be removed from the field generator 9 so that the heating material 5 no longer experiences any substantial resistive heating effect. The magnetic field generator 9 can be powered down at this stage. Optionally, the field generator 9 may be configured to automatically cease to generate the magnetic field when the predetermined volatilizing temperature has been reached and/or the predetermined heating period has elapsed.

Components of the smokable material 2 which have been volatized, or are subsequently volatized, by the heat released from the heated heating material 5 can be inhaled from the mouthpiece 4 without the field generator 9 being in the vicinity of the heating material 5. This allows a user of the apparatus 1 to inhale volatilized components from the mouthpiece 4 in a manner which is similar to how a user would inhale smokable material components from a smoking article such as a cigarette. The field generator 9 may, for example, be placed in a user's pocket for the extended period referred to above whilst the user regularly inhales newly volatilized smokable material components from the mouthpiece 4 as the smokable material 2 continues to be heated.

In all configurations of the apparatus 1, the smokable material 2 may be provided in the form of a disposable smokable material cartridge or other smokable material consumable which can be inserted into, and removed from, the heating chamber 3 via a suitable opening in the housing 8. Therefore, a user of the apparatus 1 has the option to replace the smokable material 2 in order to obtain a different or improved inhalation experience, whilst re-using the housing 8, its internal apparatus components and the field generator 9. For example, the cartridge or other consumable may comprise a hollow smokable material tube which can be slid onto and off of an elongate heating member 6, such as the one shown in FIG. 1, or may comprise a substantially solid elongate core of smokable material 2 which can be slid into and out of a hollow centre of an elongate heating member 6. The cartridge may comprise a sleeve, for example formed of plastics, which contains the smokable material 2 and from which volatilized components of the smokable material can flow into the mouthpiece 4.

Alternatively, the housing 8 and its internal components, including the smokable material 2, may together form a disposable item which is intended to be discarded by a user after use.

As shown in FIGS. 1 and 3, the housing 8 and/or the smokable material cartridge 2 may be provided with thermal insulation 14 to reduce heat losses from the smokable material 2 and the internal components of the housing 8 to the external atmosphere around the housing 8. The thermal insulation 14 may, for example, comprise vacuum insulation which is configured to insulate the apparatus 1 by providing an evacuated region between the heating chamber 3 and the external surface of the housing 8 to thereby substantially prevent heat losses by conduction and convection. The housing 8 and/or smokable material cartridge 2 may additionally or alternatively be provided with an infra-red reflective layer located between the smokable material 2 and the external surface of the housing 8 so as to prevent losses by thermal radiation. The reflective layer may optionally be provided on or in the thermal insulation layer 14.

The housing 8 may additionally or alternatively be thermally insulated by smokable material 2 located between the heating material 5 and the exterior of the housing 8.

The thermal insulation effect ensures that the external surface of the housing 8 is substantially not heated by the heating material 5 and therefore that the external surface of the housing 8 remains at a temperature which is comfortable for a user to grip the housing 8 during inhalation of volatilized components from the mouthpiece 4.

Optionally, the heating chamber 3 may be hermetically sealable so that volatilized components of the smokable material do not escape through the mouthpiece 4 undesirably. Inlet and outlet valves may be configured to seal the heating chamber 3 from the mouthpiece 4 and to only allow components which have been volatilized to leave the heating chamber 3 when a user draws on the mouthpiece 4. The apparatus 1 may include a puff sensor to trigger opening and closing of the valves at appropriate times. Alternatively, the valves may be caused to open automatically by the suction force generated by a user when he/she draws on the mouthpiece 4. A mechanical hinge may be used in the valves.

The apparatus 1 may be manufactured by dispersing the heating material 5 within a suitable base material 7 and shaping the resulting product into a heating member 6. A housing 8 of the apparatus 1 may be formed by a plastics moulding technique to provide a substantially hollow interior region into which components of the apparatus 1 can be inserted. One or more layers of thermal insulation 14 may be provided on the interior or exterior of the wall of the housing 8 in order to reduce heat losses from the heating material 5 during use of the apparatus 1. As described previously, the heating member 6 may be secured along a longitudinal axis of the housing 8, such as the central axis, so as to leave a smokable material heating chamber 3 adjacent to it. The temperature sensor 12 and timer 13, along with the indicator light or other suitable alerting unit, are also secured in the housing 8 in an appropriate position. An example is between the heating chamber 3 and the mouthpiece 4, as shown in FIG. 1. The mouthpiece 4 is provided at one end of the housing 8 and a fluid channel is provided between the heating chamber 3 and the mouthpiece 4 to allow volatilized components of smokable material 2 to flow to the mouthpiece 4 for inhalation.

In order to address various issues and advance the art, the entirety of this disclosure shows by way of illustration various embodiments in which the claimed invention(s) may be practiced and provide for a superior apparatus and method. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An apparatus to volatilize components of smokable material for inhalation, the apparatus comprising:
   a housing containing:
      a smokable material heating chamber; and
      a heating member that extends along a central longitudinal axis of the smokable material heating chamber, the heating member comprising a heat retentive base material and a plurality of separate pieces of heating material distributed throughout and in thermal contact with the heat retentive base material,
   wherein the smokable material heating chamber provides an annular space around the heating member into which smokable can be inserted for heating by the heating member, and wherein the heating material is configured to be inductively heated by a varying magnetic field to transfer heat energy to smokable material in the smokable material heating chamber to volatilize components thereof, wherein the heat retentive base material comprises a specific heat capacity that is higher than a specific heat capacity of the heating material and that is in a range of between 1,000 and 3,500 J/Kg.K so that the heat retentive base material is configured to retain heat energy received from the heating material and to transfer the heat energy to the smokable material in the smokable material heating chamber to volatilize the components.

2. The apparatus according to claim 1, wherein the heat retentive base material is configured to transfer the heat energy to the smokable material over an extended period so as to raise and maintain a temperature of the smokable material at a volatilizing temperature for the extended period without simultaneous heating of the heating material by the varying magnetic field.

3. The apparatus according to claim 1, wherein the heating material comprises an electrically conductive material.

4. The apparatus according to claim 1, wherein the heating material is susceptible to eddy currents induced by the varying magnetic field, such that, in the presence of a varying magnetic field, the eddy currents resistively heat the heating material.

5. The apparatus according to claim 1, the apparatus further comprising:
a varying magnetic field generator configured to receive the housing during heating of the heating material.

6. The apparatus according to claim 5, wherein the varying magnetic field generator is configured to releasably dock with the housing to maintain a stable position of the housing relative to the magnetic field generator during heating.

7. The apparatus according to claim 1, the apparatus further comprising a mouthpiece in fluid communication with the smokable material heating chamber and configured such that, in use, volatilized components of the smokable material are drawn through the mouthpiece by a user.

8. The apparatus according to claim 1, wherein the heating material is configured to heat the smokable material to a volatilizing temperature of between approximately 50° C. and 250° C. to volatilize the components.

9. The apparatus according to claim 1, wherein the heat retentive base material is a polymer.

10. The apparatus according to claim 1, wherein the heat retentive base material is a thermoplastic.

11. The apparatus according to claim 1, wherein the heat retentive base material is High Density Polyethylene or Polycarbonate.

* * * * *